United States Patent
Aher et al.

(10) Patent No.: US 9,302,970 B2
(45) Date of Patent: Apr. 5, 2016

(54) PROCESS FOR PREPARATION OF ALKYNYL CARBOXYLIC ACIDS

(71) Applicants: Ravindra Dattatray Aher, Pune (IN); Madhuri Hanumant Gade, Pune (IN); Reddy Santhosh Rekula, Pune (IN); Pratibha Uttam Karabal, Pune (IN); Gurunath Mallappa Suryavanshi, Pune (IN); Arumugam Sudalai, Pune (IN)

(72) Inventors: Ravindra Dattatray Aher, Pune (IN); Madhuri Hanumant Gade, Pune (IN); Reddy Santhosh Rekula, Pune (IN); Pratibha Uttam Karabal, Pune (IN); Gurunath Mallappa Suryavanshi, Pune (IN); Arumugam Sudalai, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/374,338

(22) PCT Filed: Jan. 25, 2013

(86) PCT No.: PCT/IB2013/000083
§ 371 (c)(1),
(2) Date: Jul. 24, 2014

(87) PCT Pub. No.: WO2013/110998
PCT Pub. Date: Aug. 1, 2013

(65) Prior Publication Data
US 2015/0025269 A1   Jan. 22, 2015

(30) Foreign Application Priority Data

Jan. 25, 2012 (IN) .............................. 217/DEL/2012

(51) Int. Cl.
*C07C 51/15* (2006.01)

(52) U.S. Cl.
CPC ...................................... *C07C 51/15* (2013.01)

(58) Field of Classification Search
None
See application file for complete search history.

(56) References Cited

U.S. PATENT DOCUMENTS 5,315,026 A * 5/1994 Wu ................................ 560/105

OTHER PUBLICATIONS

Joseph et al. Journal of Molecular Catalysis A: Chemical 236 (2005) 139-144.*
Dingyi et al. Green Chem., 2011, 13, 1275-1279.*
Xiao Zhang, et al., "Ligand-Free Ag(I)-Catalyzed Carboxylation of Terminal Alkynes with CO2," Organic Letters, 13(9):2402-2405 (Mar. 10, 2011).
Ravindra D. Aher, et al., "Cu-exchanged montmorillonite K10 clay-catalyzed direct carboxylation of terminal alkynes with carbon dioxide," Indian Journal of Chemistry, 51A:1325-1329 (Sep.-Oct. 2012).

* cited by examiner

Primary Examiner — Yong Chu
Assistant Examiner — Ana Z Muresan
(74) Attorney, Agent, or Firm — Abelman, Frayne & Schwab

(57) ABSTRACT

The invention provides a simple, efficient, environmentally friendly catalytic system for direct carboxylation reactions using $CO_2$ under mild conditions. A single step heterogeneous catalytic process for preparation of alkynyl carboxylic acids is disclosed.

5 Claims, No Drawings

PROCESS FOR PREPARATION OF ALKYNYL CARBOXYLIC ACIDS

RELATED APPLICATIONS

This application is a §371 of PCT/IB2013/000083 filed Jan. 25, 2013, and claims priority from Indian Patent Application No. 217/DEL/2012, filed Jan. 25, 2012, both incorporated by reference in their entirety.

TECHNICAL FIELD OF INVENTION

The present invention relates to a reproducible, environmental friendly single step heterogeneous catalytic process for preparation of alkynyl carboxylic acids. More particularly, the present invention provides a process for preparation of alkynyl carboxylic acids using heterogeneous catalytic system by carboxylation of terminal alkyne by $CO_2$ under milder reaction conditions in good yield and selectivity.

BACKGROUND OF INVENTION

Chemical Fixation of Carbon Dioxide has attracted much attention in view of environmental, legal, and social issues in the past few decades due to increasing levels of carbon dioxide. Carbon dioxide is an attractive C1 building block in organic synthesis because it is an abundant, renewable carbon source and an environmentally friendly chemical reagent. The utilization, as opposed to the storage of $CO_2$ is indeed more attractive especially if the transformation of carbon dioxide to useful bulk products is an economical one. Much research has been devoted toward exploring technologies for $CO_2$ transformation, whereby harsh and severe reaction conditions are one of the major limitations for their practical applications. Therefore, the development of efficient catalyst systems for $CO_2$ utilization under mild conditions is highly desired, especially for real world applications.

Carboxylic acids are one of the most important types of compounds in medicinal chemistry and also in fine-chemicals synthesis. Although there are many well-established protocols for the preparation of carboxylic acids, the direct carboxylation of carbon nucleophile using $CO_2$ as the electrophile is the most attractive and straightforward method. The formation of a stable C—C bond is desired for $CO_2$ fixation and remains the most challenging aspect thus far. Typically, this type of reaction is facilitated by the insertion of $CO_2$ into a metal-carbon bond in presence of organometallic reagents. Widespread use of these processes is limited by the synthesis of related organometallic reagents as precursors and the restricted substrate scope.

In the past decades, several interesting systems have been reported for metal-mediated reductive carboxylation of alkenes, alkynes to form carboxylic acids or esters. There are few methods available in the literature for direct carboxylation of terminal alkynes.

Carboxylation of terminal alkynes by using silver and copper catalyst under homogeneous conditions is known in the art.

WO2011075087 titled "Carboxylation of Terminal Alkynes" describes a process for converting a terminal alkyne into an alkynoic acid. In the process, alkyne is exposed to carbon dioxide in the presence of a copper (I) species, a base and a complexing agent such as diaminoalkene, N-heterocyclic carbene capable of complexing copper (I).

An article titled "The direct carboxylation of terminal alkynes with carbon dioxide" by Yu Dingyi; Zhang Yugen in Green Chemistry (May 2011), 13 (5), pg. 1275-1279 discloses direct carboxylation of terminal alkynes using $CO_2$ as the C1 carbon feedstock. The direct C—H bond functionalization is achieved with $Cs_2CO_3$ as the base and in the absence of transition metal catalyst. However, the process employs high pressure and temperature.

The processes in the art suffer from certain drawbacks like use of expensive or complex ligands to guarantee selectivity and catalytic efficiency. Further, the processes need either a stoichiometric amount of transition metals as reactants or an excess amount of organometallic reagents for trans metallation.

Further, as environmental regulations and safety concerns are the burgeoning issues faced by the industrial society today, development of environmentally benign methodologies remains the key issue. Among the viable alternatives available for green synthetic methods, clays and clay-based catalysts in particular have attracted significant attention due to their extremely versatile properties. Due to their structural features, they can easily be modified with different metal cations, or organic/organometallic compounds resulting in new catalysts of potential importance. Both the modified and natural clays can be applied to catalyze a broad variety of chemical transformations, thus providing exceptional importance for these materials in the development of new synthetic processes.

OBJECTIVES OF INVENTION

The main objective of the present invention is to provide a simple, efficient, environmental friendly single step process for preparation of alkynyl carboxylic acids.

Another objective of the present invention is to provide a reproducible, benign heterogeneous catalytic system for carboxylation of terminal alkynes by $CO_2$ under mild conditions to produce alkynyl carboxylic acids having varied industrial applications.

SUMMARY OF INVENTION

Accordingly, the present invention provide a single step heterogeneous catalytic process for preparation of alkynyl carboxylic acids of formula I

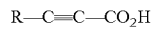
$$R-C \equiv C-CO_2H \qquad \qquad I$$

Wherein, R in the formula represents a wide range of monovalent substituents selected from a group consisting of straight or branched alkyl, straight or branched alkenyl, straight or branched alkenyloxy, straight or branched alkynyloxy, straight or branched alkenylthio, straight or branched alkynylthio, aryl, alkaryl, aralkenyl, aralkynyl, aryloxy, aralkoxy, cycloalkyl, heteroaryl, a carbonyl, where each of these may be substituted with halo, hydroxyl, nitro, amino, cyano, alkoxy, carboxyl, ester, alkyl, alkenyl, alkynyl, thio, sulfonyl, sulfinyl, phenyl, heteroaryl or a carbonyl by carboxylation of terminal alkyne with $CO_2$, wherein the said process comprising, reacting terminal alkynes of formula II

$$R-C \equiv C-H \qquad \qquad II$$

with carbon dioxide in the presence of a heterogeneous catalyst, a base and a solvent at temperature ranging between 50-60.degree. C. for a period ranging between 12-16 hrs under pressure about 1 atm to obtain desired product of formula I.

In one embodiment of the present invention the heterogeneous catalyst is metal exchanged montmorillnite K-10 clay catalyst.

In another embodiment of the present invention the metal is selected from group 11 or group 8 of the periodic table.

In still another embodiment of the present invention the metal is preferably copper in the range of 10-30 w/w %.

In yet another embodiment of the present invention the base for the reaction is selected from organic or inorganic bases.

In yet another embodiment of the present invention said base is selected from the group consisting of di-ethylamine, tri-ethylamine, sodium methoxide, sodium ethoxide, carbonates or phosphates of alkali and alkaline metals such as potassium carbonate, sodium carbonate, cesium carbonate, $K_3PO_4$ preferably cesium carbonate ($Cs_2CO_3$).

In yet another embodiment of the present invention the base is used in the range of 1-2 equivalents.

In yet another embodiment of the present invention the solvent is polar aprotic solvent selected from the group consisting of Dimethylformamide (DMF), Tetrahydrofuran (THF), Acetonitrile (MeCN), Dimethyl sulfoxide (DMSO), Dichloromethane (DCM).

In yet another embodiment of the present invention yield of alkynyl carboxylic acids of formula I is in the range of 70-94%.

In yet another embodiment of the present invention selectivity of alkynyl carboxylic acids of formula I is 100%.

DETAILED DESCRIPTION OF INVENTION

The present invention provides a simple, efficient, reproducible, environmental friendly M(II) exchanged montmorillonite K-10 catalyst for the direct carboxylation reaction of compound of formula II using $CO_2$ in presence of base and solvent to obtain functionalized alkynyl carboxylic acids of general formula I in good yield and selectivity.

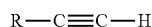
(II)

(I)

Wherein, R is described herein below.

The group R in the formula represents a wide range of monovalent substituents selected from a group consisting of straight or branched alkyl, straight or branched alkenyl, straight or branched alkynyl, straight or branched alkenyloxy, straight or branched alkynyloxy, straight or branched alkenylthio, straight or branched alkynylthio, aryl, alkaryl, aralkenyl, aralkynyl, aryloxy, aralkoxy, cycloalkyl, heteroaryl, a carbonyl, where each of these may be substituted with halo, hydroxyl, nitro, amino, cyano, alkoxy, carboxyl, ester, alkyl, alkenyl, alkynyl, thio, sulfonyl, sulfinyl, phenyl, heteroaryl or a carbonyl.

The terminal alkyne is represented by a formula R—C≡C—H, where R in the formula represents a wide range of monovalent substituents selected from a group consisting of straight or branched alkyl, straight or branched alkenyl, straight or branched alkynyl, straight or branched alkenyloxy, straight or branched alkynyloxy, straight or branched alkenylthio, straight or branched alkynylthio, aryl, alkaryl, aralkenyl, aralkynyl, aryloxy, aralkoxy, cycloalkyl, heteroaryl, a carbonyl, where each of these may be substituted with halo, hydroxyl, nitro, amino, cyano, alkoxy, carboxyl, ester, alkyl, alkenyl, alkynyl, thio, sulfonyl, sulfinyl, phenyl, heteroaryl or a carbonyl.

The product R—C≡C—$CO_2H$ in the instant invention are at times referred to as "alkynyl carboxylic acids", "propiolic acids", "functionalized propiolic acids", "alkynoic acids" "propynoic acids". In certain embodiments, these acids may be present in the form of salts of organic or inorganic acids.

In an embodiment, the present invention provides an efficient direct carboxylation of terminal alkynes, R—C≡C—H, with carbon dioxide in the presence of reproducible, environmental friendly M(II) exchanged montmorillonite K-10 catalyst, a base and a solvent to obtain alkynyl carboxylic acids of general formula R—C≡C—$CO_2H$ in good yield and selectivity.

In the catalyst, M(II) exchanged montmorillonite K-10, 'M' represents metal ion selected from group 11 such as Cu, Ag, Au etc or from group 8 such as Ru, Os, etc, preferably the metal is copper, in the range of 10-30 w/w %. The M(II) exchanged montmorillonite K-10 are prepared by the method known in the art.

Organocopper reagents are very unique because the metal-carbon bond is of moderate polarity and is ready for $CO_2$ insertion under ambient conditions, and they are also tolerant to most functional groups. Copper catalysts can also catalyze various C—H and C-halogen activation reactions, and many of them involve intermediates with a Cu—C bond. These facts make copper catalysts thus make a very promising choice for $CO_2$ transformation, especially with the formation of new C—C bonds like oxidative homocoupling of terminal alkynes via C—H activation.

The base for the reaction is selected from organic or inorganic bases. The organic base includes diethylamine, triethylamine, sodium methoxide, sodium ethoxide etc. The inorganic bases are selected from carbonates or phosphates of alkali and alkaline metals such as potassium carbonate, sodium carbonate, cesium carbonate, $K_3PO_4$ etc; preferably the base is cesium carbonate ($Cs_2CO_3$). The base is used in the range of 1-2 equivalent.

The solvent is selected from polar aprotic solvent such as DMF, THF, MeCN, DMSO, DCM etc. Optionally, other supports are used in the reaction selected from hydrotalcite and zeolites. To indicate the effectiveness of the heterogeneous catalyst system for direct carboxylation of terminal alkynes, an initial experiment was conducted using 1-ethynylbenzene (1a) as a model compound in the presence of $Cs_2CO_3$ (1.5 mmol), Cu(II) montmorillonite K-10 (10 w/w %). Accordingly, compound 1a (1 mmol) is treated with $CO_2$ (1 atm) in N,N-dimethylformamide (DMF) at 60° C. for 12 h with subsequent acid hydrolysis to obtain 3-phenylpropiolic acid (1b). the reaction is depicted in Scheme 1.

Scheme 1

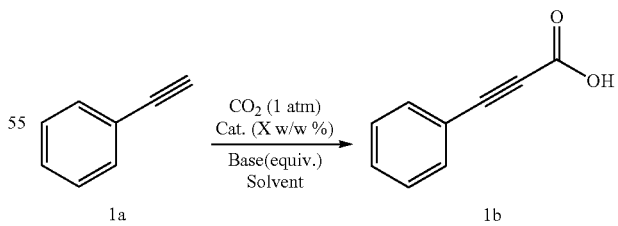

The reaction conditions are further investigated by varying metal catalyst, bases, and solvent systems for catalytic carboxylation of terminal alkyne with $CO_2$ in good yields and 100% selectivity. The best result are obtained with 30 w/w % Cu(II) montmorillonite K-10 catalyst and 1.5 equivalent $Cs_2CO_3$ as base in DMF solvent as given in Scheme 2 and Table 1.

Scheme 2

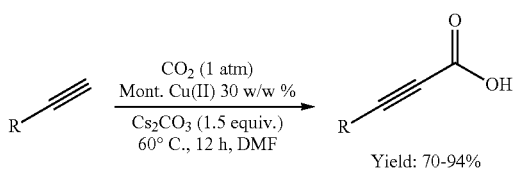

Yield: 70-94%

According to Scheme 2, terminal alkynes and $Cs_2CO_3$ are added to DMF in a two-necked RB flask. Then clay catalyst is added (20 w/w %) and $CO_2$ is then introduced into the reaction mixture under stirring. The reaction mixture is stirred at 50-60° C. for 14 h under 1 atm. After completion of the reaction, the reaction mixture is cooled to room temperature and transferred to the potassium carbonate solution under stirring for 30 min. The mixture is washed with dichloromethane and the aqueous layer is acidified with concentrated HCl to pH=1, extracted with diethyl ether. The combined organic layers are dried, filtered and the solution is concentrated in vacuum to obtain pure product.

Table 1 below describes the conditions screening for Catalytic carboxylation of 1-ethynylbenzene with $CO_2$. (Temperature 60° C., 14 h, 1 atm)

| Entry | Catalyst (w/w %) | Base (equiv.) | Solvent | Yield (%) |
|---|---|---|---|---|
| 1 | — | $Cs_2CO_3$ (1.5) | DMF | 0 |
| 2 | Mont.K10 (10) | $Cs_2CO_3$ (1.5) | DMF | 5 |
| 3 | Mont.$Cu^{II}$ (10) | $Cs_2CO_3$ (1.5) | DMF | 60 |
| 4 | Mont.$Cu^{II}$ (20) | $Cs_2CO_3$ (1.5) | DMF | 65 |
| 5 | Mont.$Cu^{II}$ (30) | $Cs_2CO_3$ (1.5) | DMF | 94 |
| 6 | Mont.$Cu^{II}$ (20) | $K_2CO_3$ (2) | DMF | 0 |
| 7 | Mont.$Cu^{II}$ (10) | $Cs_2CO_3$ (1.5) | MeCN | 10 |
| 8 | Mont.$Cu^{II}$ (10) | $Cs_2CO_3$ (1.5) | DMSO | 8 |
| 9 | Mont.$Cu^{II}$ (10) | $Cs_2CO_3$ (1.5) | THF | 0 |
| 10 | Mont.$Cu^{II}$ (10) | $Et_3N$ (1.5) | DMF | 0 |
| 11 | Mont.$Cu^{II}$ (10) | DBU (1.5) | DMF | 29 |
| 12 | Mont.$Cu^{II}$ (10) | DBU (2.5) | DMF | 45 |
| 13 | Mont.$Ag^{I}$ (10) | $Cs_2CO_3$ (1.5) | DMF | 14 |
| 14 | Mont.$Ag^{I}$ (10) | DBU(1.5) | DMF | 8 |
| 15 | Mont.$Cu^{II}$—$Pd^{II}$ (10) | $Cs_2CO_3$ (1.5) | DMF | 10 |
| 16 | Mont.$Cu^{II}$—$Pd^{II}$ (10) | DBU(1.5) | DMF | 13 |
| 17 | Mont.$Ru^{III}$ (10) | $Cs_2CO_3$ (1.5) | DMF | 7 |
| 18 | Mont.$Ru^{III}$ (10) | DBU(1.5) | DMF | 15 |

The catalytic carboxylation of terminal alkynes according to the instant invention are tolerated by various functional groups like halides, alkoxy groups as depicted in Table 2.

TABLE 2

Catalytic carboxylation of terminal alkynes

| Sr. No. | Substrate | Product | % Yield |
|---|---|---|---|
| 1 | phenylacetylene | phenylpropiolic acid | 94 |
| 2 | 4-methylphenylacetylene | 4-methylphenylpropiolic acid | 72 |
| 3 | 4-phenyl-1-butyne | 5-phenyl-2-pentynoic acid | 90 |
| 4 | (2-phenethoxy)propyne | (2-phenethoxy)propynoic acid | 85 |

TABLE 2-continued

Catalytic carboxylation of terminal alkynes

| Sr. No. | Substrate | Product | % Yield |
|---|---|---|---|
| 5 | | | 82 |
| 6 | | | 80 |

Reaction condition:—Alkyne (3.0 mmol), $Cs_2CO_3$ (6 mmol), DMF (15 mL), clay catalyst, (30 w/w %), 60° C., 14 h, $CO_2$ 1 atm (balloon).

Due to the heterogeneous conditions, the present inventor advantageously has recovered the catalyst by simple filtration and successfully reused it three times without losing its activity. In summary, the inventors have successfully developed a transformation of $CO_2$ to carboxylic acid, having varied industrial and pharmaceutical applications, through C—H bond activation and carboxylation of terminal alkynes. This is achieved using an efficient, benign, environmental friendly heterogeneous catalytic system. The process is carried out under mild conditions and the catalytic system is active to a wide range of aliphatic and aromatic terminal alkynes. Thus various propiolic acids are prepared in excellent yield and selectivities. The process therefore has great potential for practical application.

The invention can be better understood by the following non-limiting examples. The examples given are mere an illustration of the instant invention and should not be construed as limiting the scope of the present invention in any manner.

General Experimental Procedure

Example 1

Preparation of Cu (II) Exchanged Montmorillnite K-10 Clay

All the metal exchanged montmorillonite K10 clay catalysts were prepared and characterized following the reported procedures. For example, $Cu^{II}$-Mont. K10 clay was prepared by slurring acidic clay Mont. K-10 (10 g) [purchased from Aldrich, USA] dried at 100° C. overnight with 0.5M aqueous solution of $Cu(CH_3CO_2)_2$ (50 ml) at 90° C. for 8 h and then cooled to room temperature and filtered. This process was repeated once to ensure maximum copper metal ion exchange. The solid obtained was filtered and washed several times with water and dried at 100° C. for 12 h and then calcined (300° C. for 4 h). The copper content of the $Cu^{II}$-Mont. K10 clay catalyst was measured by AAS and found to be 0.9 mmol/g. The XRD profile of mont. K10 showed a layered structure with basal spacing ($d_{001}$) of 3.34 Å. After treatment with $Cu(CH_3CO_2)_2$ the XRD studies of $Cu^{II}$-Mont. K10 showed a layered structure is retained and the basal spacing of ($d_{001}$) was estimated to be 3.35 Å, which comparable to the parent K10.

Metal exchanged clay catalyst was prepared by using the literature methods. For example, Cu(II) exchanged Mont.K10 clay catalyst was prepared by treating Mont.K10 clay (2 g) with 25 ml aqueous Cu $(NO_3)_2$ (1 M) under vigorous stirring at room temperature for 24 h, centrifuging and washing the Cu exchanged clay with distilled deionized water repeatedly until the discarded filtrate was free from $Cl^-$ and $NO^{3-}$ ions, and drying the resulting mass at 110° C. for 12 h.

Example 2

General Procedure for Carboxylation of the Terminal Alkynes with Cu-Clay Catalyst Terminal alkynes (3.0 mmol) and $Cs_2CO_3$ (6 mmol) were added to the DMF (15 mL) in a two-necked RB (25 mL). Then clay catalyst Cu (II) exchanged montmorillnite K-10 clay (30 w/w %) was added $CO_2$ (30 bubbles/min) was then introduced into the reaction mixture under stirring. The reaction mixture was stirred at 60° C. for 14 h under 1 atm. After completion of the reaction, the reaction mixture was cooled to room temperature (25° C.) and transferred to the potassium carbonate solution (2 N, 5 mL) under stirring for 30 min. The mixture was washed with dichloromethane (3×5 mL) and the aqueous layer was acidified with concentrated HCl to pH=1, then extracted with diethyl ether (3×5 mL). The combined organic layers were dried with anhydrous $Na_2SO_4$, filtered and the solution was concentrated in vacuum affording pure product, which confirmed by NMR, IR and elemental analysis.

Example 3

3-Phenylpropiolic acid (1): Terminal alkyne:—1-ethynylbenzene

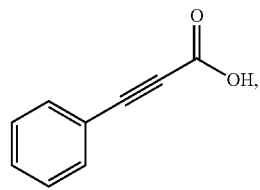

Yield: 94%, 100% selectivity 1H NMR (200 MHz, CDCl₃): δ=8.35 (s, 1H), 7.39-7.65 (m, 5H). 13C NMR (200 MHz, CDCl₃): δ=158.69, 133.31, 131.10, 128.66, 119.22, 88.91, 80.24. IR (cm$^{-1}$) (neat) 2201.62, 1673.17. Anal. Calcd for $C_9H_6O_2$ requires C, 73.97; H, 4.14%. found C, 73.95; H, 4.14%.

Example 4

4-Methylphenylpropiolic acid (2) Terminal alkyne:—1-ethynyl-4-methylbenzene

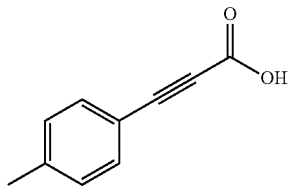

Yield: 72%, 100% selectivity 1H NMR (200 MHz, CDCl₃): δ=10.55 (br s, 1H) 7.52 (d, J=8.0 Hz, 2H), 7.21 (d, J=8.0 Hz, 2H), 2.39 (s, 3H). 13C NMR (200 MHz, CDCl₃): δ=158.62, 141.75, 133.36, 129.46, 116.17, 89.43, 79.8, 21.84. IR (cm–1) (neat) 2195.22, 1673.27. Anal. Calcd for $C_{10}H_8O_2$ requires C, 74.99; H, 5.03%. found C, 74.97; H, 5.05%.

Example 5

5-phenylpent-2-ynoic acid (3) Terminal alkyne:—1-(but-3-ynyl)benzene

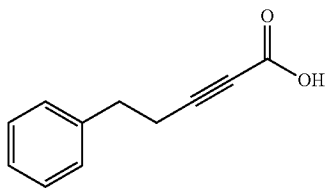 [SMILES: O=C(O)C#CCCc1ccccc1]

Yield: 90%, 100% selectivity 1H NMR (200 MHz, CDCl₃): δ=6.22 (br s, 1H), 7.18-7.34 (m, 5H), 2.64 (t, 2H), 2.90 (t, 2H). 13C NMR (200 MHz, CDCl₃): δ=157.82, 139.35, 128.61, 128.32, 126.73, 90.92, 73.41, 33.71, 20.96. IR (cm–1) (neat) 2238.09, 1701.03 Anal. Calcd for $C_{11}H_{10}O_2$ requires C, 75.84; H, 5.79%. found C, 75.85; H, 5.78%.

Example 6

4-(phenethyloxy) but-2-ynoic acid (4) Terminal alkyne:—1-(2-(prop-2-ynyloxy)ethyl)benzene

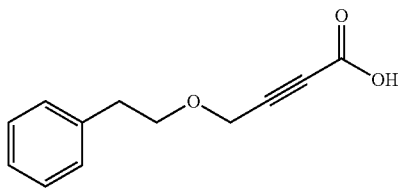 [SMILES: O=C(O)C#CCOCCc1ccccc1]

Yield: 85%, 100% selectivity 1H NMR (200 MHz, CDCl₃): δ=6.22 (br s, 1H), 7.18-7.34 (m, 5H), 2.64 (t, 2H), 2.90 (t, 2H). 13C NMR (200 MHz, CDCl₃): δ=157.99, 139.50, 128.70, 128.34, 126.75, 92.92, 81.01, 74.41, 33.71, 20.96. IR (cm-1) (neat) 2240.09, 1712.03 Anal. Calcd for $C_{12}H_{12}O_3$ requires C, 70.57; H, 5.92%. found C, 70.58; H, 5.91%.

Example 7

4-(p-tolyloxy) but-2-ynoic acid (5) Terminal alkyne:—1-methyl-4-(prop-2-ynyloxy)benzene

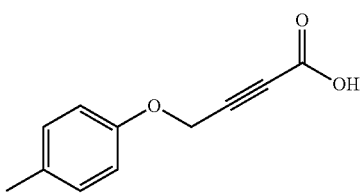

Yield: 82%, 100% selectivity 1H NMR (200 MHz, CDCl₃): δ=6.10 (br s, 1H), 6.83-6.87 (d, J=8.0 Hz, 2H), 7.08-7.12 (d, J=8.0 Hz, 2H) 2.31 (s, 2H), 4.80 (s, 2H). 13C NMR (200 MHz, CDCl₃): δ=156.86, 155.14, 131.45, 130.09, 115.01, 84.78, 78.00, 55.65, 20.57. IR (cm–1) (neat) 2251.21, 1690.10. Anal. Calcd for $C_{11}H_{10}O_3$ requires C, 69.46; H, 5.30%. found C, 69.48; H, 5.29%.

Example 8

6-chlorohex-2-ynoic acid (6) Terminal alkyne:—5-chloropent-1-yne

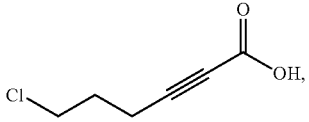

Yield: 80%, 100% selectivity 1H NMR (200 MHz, CDCl₃): δ=6.63 (br s, 1H), 3.64 (t, J=6.0 Hz, 2H), 2.57 (d, J=6.0 Hz, 2H), 2.08 (quin, 2H). 13C NMR (200 MHz, CDCl₃): δ=157.21, 89.50, 75.6, 43.03, 30.07, 16.06. IR (cm–1) (neat) 2239.48, 1700.99. Anal. Calcd for $C_6H_7ClO_2$ requires C, 49.17; H, 4.81; Cl, 24.19%. found C, 49.19; H, 4.80; Cl, 24.20%.

ADVANTAGES OF THE CURRENT INVENTION

Employs economic heterogeneous catalytic process

Catalysts are stable under thermal and air

Catalyst can be recovered and reused for several times without losing its activity All reactions performed at ambient conditions with greater selectivity and yields This procedure tolerates a series of functional groups, such as alkoxy, fluoro and chloro, etc.

It represents a procedure for the synthesis of varied propiolic acids.

We claim:

1. A process for preparation of an alkynyl carboxylic acid of formula:

R—C≡CO₂H wherein R is a monovalent substituent selected from the group consisting of straight or branched alkyl, straight or branched alkenyl, straight or branched alkenyloxy, straight or branched alkynyloxy, straight or branched alkenylthio, straight or branched alkynylthio, aryl, alkaryl, aralkenyl, aralkynyl, aryloxy, aralkoxy, cycloalkyl, heteroaryl, and a carbonyl, where each of these may be substituted with halo, hydroxyl, nitro, amino, cyano, carbonyl, alkoxy, carboxyl, ester, alkyl, alkenyl, alkynyl, thio, sulfonyl, sulfinyl, phenyl or heteroaryl by carboxylation of terminal alkyne with $CO_2$, wherein said process comprises reacting a terminal alkyne of formula:

R—C≡C—H wherein R is as above with carbon dioxide, in the presence of a heterogeneous copper(II) exchanged montmorillonite K-10 catalyst, cesium carbonate ($Cs_2CO_3$) as a base and DMF as a solvent at temperature ranging between 50-60° C. for a period ranging between 12-16 h under a pressure of about 1 atm to obtain a compound of formula

R—C≡C—CO₂H.

2. The process according to claim 1, wherein the heterogeneous copper(II) exchanged montmorillonite K-10 catalyst is present in a range of 10-30 w/w %.

3. The process according to claim 1, wherein the base is used in the range of 1-2 equivalents.

4. The process according to claim 1, wherein yield of said alkynyl carboxylic acids is in the range of 70-94%.

5. The process according to claim 1, wherein selectivity of catalyst for said alkynyl carboxylic acid is 100%.

* * * * *